Figure 1:
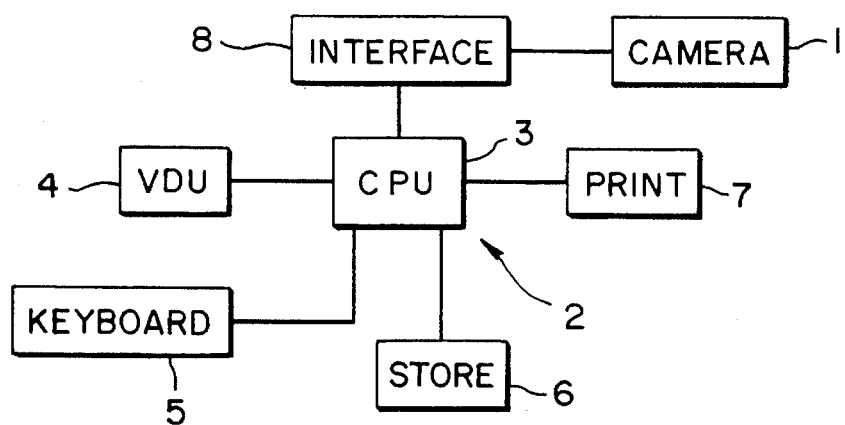

United States Patent
Salisbury

[11] Patent Number: 5,483,604
[45] Date of Patent: Jan. 9, 1996

[54] MONITORING CHANGES IN IMAGE CHARACTERISTICS

[75] Inventor: Richard Salisbury, Littlebury, United Kingdom

[73] Assignee: Thermoteknix Systems Ltd., Cambridge, United Kingdom

[21] Appl. No.: 317,842

[22] Filed: Oct. 4, 1994

Related U.S. Application Data

[63] Continuation of Ser. No. 19,703, Feb. 19, 1993, abandoned.

[30] Foreign Application Priority Data

Feb. 20, 1992 [GB] United Kingdom .................. 9203583

[51] Int. Cl.⁶ ..................................................... G06K 9/00
[52] U.S. Cl. ........................................ 382/152; 382/194
[58] Field of Search ....................... 382/44, 8, 46, 382/1, 34, 141, 152, 209, 218, 294; 348/92, 87, 125, 126, 129, 130; 374/124, 120

[56] References Cited

U.S. PATENT DOCUMENTS

| | | | |
|---|---|---|---|
| 3,748,644 | 7/1973 | Tisdale | 382/74 |
| 4,193,302 | 3/1980 | Nixon | 394/124 |
| 4,288,852 | 9/1981 | Holland | 382/8 |
| 5,032,727 | 7/1991 | Cox, Jr. et al. | 382/1 |
| 5,038,393 | 8/1991 | Nanby | 382/46 |
| 5,059,796 | 10/1991 | Nuhamora | 382/1 |
| 5,077,811 | 12/1991 | Onda | 382/44 |
| 5,163,094 | 11/1992 | Prokoski et al. | 382/1 |
| 5,175,772 | 12/1992 | Kahn et al. | 382/8 |
| 5,189,625 | 2/1993 | LeFloch | 382/8 |
| 5,309,108 | 5/1994 | Maeda et al. | 382/8 |

*Primary Examiner*—Joseph Mancuso
*Attorney, Agent, or Firm*—Fisher, Christen & Sabol

[57] ABSTRACT

Changes in characteristics of an image are monitored at a predetermined position or zone (12, 13) of the image. The image is corrected to allow for changes in the monitored position or zone (12, 13). This is done with reference to observed deviation in coordinates of reference points (9–11) of the image. In a preferred embodiment, successive thermographic images are obtained of electronic equipment, such as a printed circuit board, and the image as displayed on a VDU screen (4) is scanned at a predetermined point (12) or along a predetermined line (13) to monitor temperature-dependent color characteristics of the image, whereby the development of hotspots can be monitored. Changes in the coordinates of landmark positions (9–11) on the image are noted and are used to correct the positions of successive images on the screen so that the monitored point (12) or line (13) is always in the same position. This correction is achieved by transformation of data using spread sheet software.

11 Claims, 1 Drawing Sheet

MONITORING CHANGES IN IMAGE CHARACTERISTICS

This application is a continuation of prior U.S. application Ser. No. 08/019,703 filing date Feb. 19, 1993 now abandoned.

This invention relates to the monitoring of image characteristics for condition monitoring purposes.

It is known to monitor the condition of subjects by examination of images. Thus, for example, the condition of electrical and mechanical components, equipment, plant, and physical structures such as buildings or bridges, can be monitored for failure in insulation, lamination or thermal conduction using infrared thermography.

An infra-red image of the subject is generated and this is examined as a single diagnostic event or as part of a series of images generated at different times.

In the case of a single diagnostic event, temperature over the image can be measured to show a variation from that of related components or from ambient temperature or from predicted or expected values, so that immediate identification of a fault or malfunction or potential failure can be made.

In the case of a series of images, temperature measurements are made over a period of time and the results are assessed to reveal a progressive or sudden change. The change is used to predict maintenance or to identify a failure or local fault. Assessment of change may be made by means of an extracted value from the image, and this value may be a direct measurement or an indirect quantification based on a pattern or distribution such as a standard deviation.

It is possible to apply similar condition monitoring techniques to images other than infrared thermographs. For example, ultrasonics, video, vibration analysis, radiography, nuclear magnetic resonance imaging may be used.

There is the problem with known techniques that it may be difficult to recognise individual features in the image, or, in the case where successive images are compared to achieve accurate registration or alignment of features. In this respect, monitoring surveys are commonly carried out with portable instruments and with such an instrument it is difficult to obtain an image which accurately has a desired registration.

Variations in registration can be minimised in some cases by means of a physical assembly or fixture, but this is not always practicable especially for larger plant or fixed installations. It is also possible to use locating markers to assist siting of the imaging equipment or to help the user of the equipment in achieving alignment. However, this may not always be possible, for example in the case of an aerial survey where the imaging equipment is mounted in a helicopter or aeroplane or the like.

The problem is exacerbated in the case where a two dimensional image is derived from a three dimensional subject. Registration errors will occur if there is any variation in the X, Y or Z dimension.

Registration errors reduce the ability for accurate image comparison, automated analysis, or difference measurements. Furthermore, a measurement made on the image at a given screen coordinate position will not correspond to the same physical location on the same subject when it is viewed from a different position.

An object of the present invention is to provide an improved image monitoring technique whereby the above problems associated with the identification and registration of image features can be overcome or at least minimised.

According to the invention therefore there is provided a method of monitoring changes in image characteristics comprising the steps of generating an image of a subject using imaging equipment; determining coordinates of reference points on said image; monitoring characteristics of a predetermined position or zone of said image relative to said coordinates; and comparing said determined characteristics with predetermined reference characteristics; characterised by the steps of determining any deviation between the determined coordinates of the reference points and predetermined coordinates thereof, and correcting for the deviation in effecting the said monitoring of characteristics of the predetermined position or zone.

With this arrangement, in effect, a misaligned image can be brought into registration before it is examined for condition monitoring purposes. Images can be standardised and analysed after having been corrected for variations in disposition between the subject, imaging equipment and the user of such equipment or observer. Thus, measurement of the distance or distances from the imaging equipment to a two or three dimensional subject and the relative angles of view need not be made and direct spacial measurements from the image can be obtained from the image in 'real world' coordinates i.e. distances between parts of the image in meters rather than in pixels.

The method may be applied to a single event technique where a single image is obtained and the reference points are related to predetermined such points and the changes in the monitored characteristics are determined relative to predetermined characteristics derived e.g. from ambient characteristics or predicted characteristics or the like.

Alternatively and preferably however successive images are obtained at different times, the reference points on each successive image are related to predetermined points on the previous image or images, and the changes in monitored characteristics on each successive image are determined relative to the characteristics for the previous image or images.

Thus, and in accordance with a second aspect of the present invention there is provided a method of monitoring changes in image characteristics comprising the steps of:

generating a first image of a subject;

determining coordinates of reference points on said image;

determining predetermined characteristics of a predetermined position or zone of said image relative to said coordinates;

generating a second image of the subject;

determining coordinates of the said reference points on the said second image;

comparing the said coordinates for the first and second images to determine a difference therebetween;

identifying the location of the said predetermined position or zone on the second image by reference to the location thereof on the first image and the said coordinates difference; and comparing the said predetermined characteristics of the said predetermined position or zone for the first and second images to determine a difference therebetween.

In practice the method of the invention will preferably be performed with computer apparatus incorporating a screen on which an obtained image is visually displayed in conjunction with a cursor or pointer arrangement for locating the said reference points, and establishing the coordinates thereof, on the displayed image.

Most preferably the arrangement is such that the image is automatically visually re-aligned on the screen, after the coordinates of the reference points have been established, to bring such reference points accurately into registration with the predetermined coordinates thereof.

The said characteristics of the corrected image can be monitored in any suitable manner. This could be done visually e.g. by identification of points or zones of colour change indicating hot spots or the like. Preferably however the image or zones or points thereof are scanned to permit automatic monitoring of temperature changes or other variations in characteristics. For example, using a cursor or pointer or the like a line may be identified on the image and variations in characteristics along the line may be calculated. There may be an automatic output of appropriate data in the form of a graph, or lists of numbers which may be shown as a screen display or which may be printed out. Where provision is made for an automatic hard copy print-out, this may also include printed pictures of the image. The above mentioned equipment may also include word processing, database, or similar software.

The above mentioned correction or image transformation steps to compensate for deviations in the coordinates of the reference points are preferably effected on a discrete area-by-area or pixel-by-pixel basis. Similarly, monitoring of characteristics and determination of changes is preferably also done on a discrete area-by-area or pixel-by-pixel basis. Conveniently, in this case, spread sheet software may be used, i.e. software permitting entry of numerical data into individual cells with provision being made for automatic computations to be made on such numerical data in accordance with predetermined mathematical relationships or equations for each cell. This provides a convenient means of processing data whilst storing the data in readily accessible and readily utilisable form. Thus in addition to transforming and monitoring changes in the characteristics of the image the spread sheet provides a means of storing image data for subsequent retrieval and also can easily interface with wordprocessor or similar software to facilitate production of screen displays and hard copy print-outs.

Thus, and in accordance with a yet further aspect of the present invention there is provided a method of monitoring changes in image characteristics comprising the steps of obtaining an image of a subject using imaging equipment, deriving data from the image in discrete units, storing said data, transforming said stored data to correct for deviations in image coordinates, monitoring changes in said transformed stored data, and producing an output representative of such data changes, wherein the data is stored, and processed using spread sheet software.

The invention also provides apparatus for use in performing the above described methods comprising imaging equipment for producing data representative of an image of a subject, computer equipment for storing and processing said data, said computer equipment including a screen arranged to display said image, cursor means arranged for identifying reference points on the displayed image and to establish coordinates of said points, monitoring means arranged for monitoring characteristics of the image at a predetermined point or zone thereon, comparing means arranged for comparing said characteristics with predetermined reference characteristics; and deviation means arranged for determining any deviation between the determined coordinates of the reference points and predetermined coordinates thereof and for correcting for the deviation in effecting the said monitoring of characteristics of the predetermined position or zone.

The imaging equipment may be infrared thermography equipment using an ir sensor. However, other kinds of equipment using different kinds of sensors may also be used.

The method and apparatus of the invention may be used for condition monitoring in any suitable context and for any suitable purpose. The invention can be applied to the development of hot spots in electrical or electronic equipment or plant components or the like. However the invention is not restricted to this.

Figure 2:
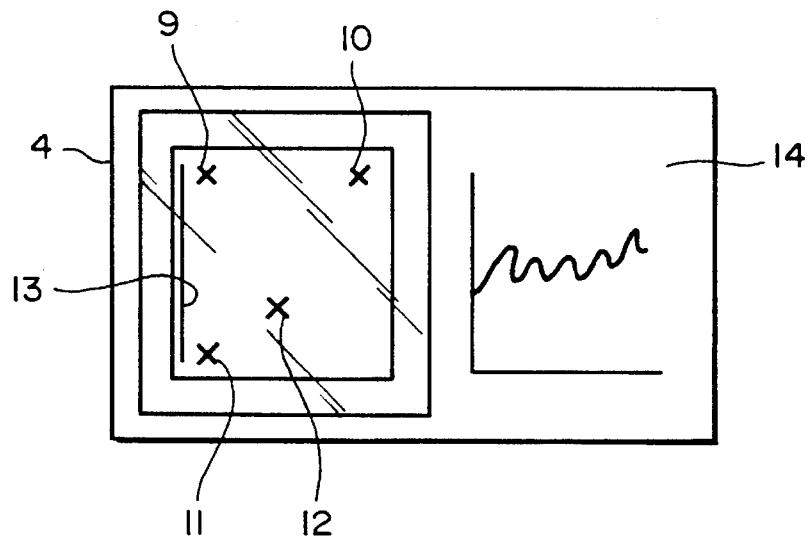
Figure 3:
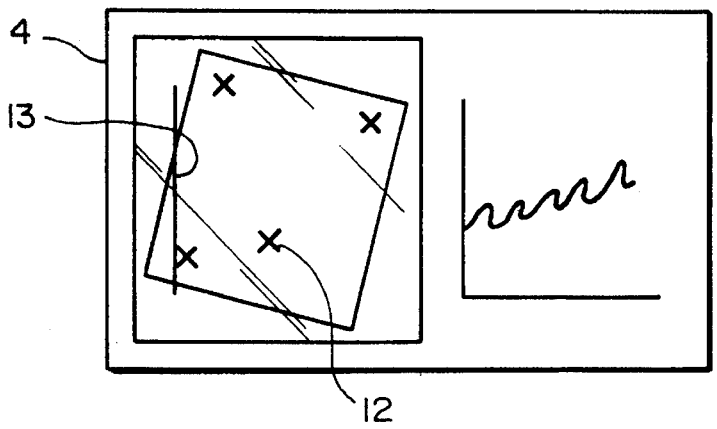

The invention will now be described further by way of example only and with reference to the accompanying drawings in which:

FIG. 1 is a schematic representation of one form of apparatus according to the invention; and FIGS. 2 & 3 are two screen displays obtained with the apparatus of FIG. 1.

The apparatus shown in FIG. 1 comprises a conventional portable infrared thermography camera 1, and a computer system 2 having a programmed central processor 3, a VDU screen 4, a keyboard 5, a memory store 6, a printer 7, and an interface 8 for input of data.

In use, an infrared 'picture' is taken with the camera for example of a printed circuit board the condition of which is being monitored in equipment in a factory or other plant or installation.

The 'picture' is in the form of image-generating data. This data is transferred to the computer system 2 in conventional manner via the interface 8.

A quantised (digital) image is displayed on the screen 4. Three recognisable features 9, 10, 11 are identified on the image. These may be natural landmarks on the subject (e.g. specific components on the printed circuit board) or reference markers pre-placed to assist feature identification.

The X, Y screen coordinates of each feature 9, 10, 11 are stored by moving a cursor (or cross or spot) across the screen (e.g. with a mouse) until it is on top of the respective feature and then operating a control (e.g. a mouse button or keyboard key) to cause the coordinates to be entered.

A further cursor 12 (or cross or spot) is similarly moved to overlie a point on the printed circuit board which is to be given special attention because it is, or is likely to, overheat. A cursor line 13 is moved to a position across the board along which the temperature is to be monitored. The coordinates of the further cursor 12 and the cursor line 13 are also entered.

By assessment of the digital data at the coordinates of point 12 and along the line 13 the temperature of the respective regions of the printed circuit board is determined, in conventional manner.

A graph 14 of temperature against location (pixels on the screen) can be displayed on the screen alongside the thermal image.

The above procedure is repeated for a second image of the same printed circuit board obtained subsequently with a view to monitoring condition changes over a period of time.

As shown in FIG. 3, the second image, as obtained, is not precisely aligned with the first image. This is corrected by placing the cursors 9, 10, 11, over the markers or landmark features on the image and entering the X, Y coordinates. These X, Y coordinates are compared with the previously entered coordinates and the difference is computed. This difference is used to perform a perspective transformation on the mis-aligned second image, pixel-by-pixel. The data stored for the image is changed to 'corrected' data and, correspondingly, the image on the screen is moved so that the image appears in the same position and with the same perspective as the first image.

The image is transformed to the absolute positional placement of the subject in space (or real world). The temperature at the cursor point 12 and along the line 13 can then be measured and compared with the previous values. Trends can therefore be identified and predicted and a report can be printed out using the printer 7.

The procedure can be repeated for further, successive images. In more detail, the above procedure is performed as follows:

Perspective transformation to ensure that each successive image is correctly aligned with the initial reference image is performed as follows: The transformation maps pixel positions in the images file to real world positions using linear scaling in the X and Y directions. Thus a general pixel x,y is mapped to a world position X, Y by a relationship:

$$X=a*x+b*y+c$$

$$Y=d*x+e*y+f$$

where a, b, c, d, e and f are constants that characterise the transformation. If the image is considered to be a plane this transformation will compensate for changes in perspective between the world coordinate axis and the pixels of the image i.e. changes in the position of the camera. In the software the image is transformed to display on the screen with the world perspective i.e. with the X and Y world axes orthogonal. The transformation is fully defined by locating three corresponding positions in the two coordinate systems. Once the three positions have been identified and the corresponding points in the real world established, the link to real world positions is defined for all pixels in the image. The above may be used to directly calibrate the X and Y positions in the real world e.g. link the image to real measurements made in suitable units. However it may also be used to convert the view of an image to the perspective viewpoint of an earlier image of the same object. The requirement here is simply that the same three points are picked out of each image and the same corresponding three world positions are entered. The world positions are arbitrary and for simplicity the pixel positions from the first image can be used as world coordinates and are entered for the corresponding points on the second image. Again location identified with real world coordinates will be mapped to corresponding positions in the pixel data. In this way features identified in the first image will also be picked out on the second image.

Measurement tools of image content such as Max, Min, Mean value within specified areas, profile intensities along a line in the image or histogram types of analysis of samples within a defined area, can then be made at required locations on the image and the results together with the details and positions of the measurement tools stored in a data file. Settings for the operating, measurement and image display parameters can also be recorded in the file with text labels or comments. The settings file is stored as a named template either as a data file or in the form of a spreadsheet.

By the use of a spreadsheet file to record the image settings and extracted data, values are available for ease of re-analysis without the parent image, or their incorporation into reports. The data is also readily available for archiving, data base manipulation or further processing.

When a second or subsequent image of the same or similar object is analysed, the image is displayed on screen and the named template file is restored. The three location cursors are shown on the screen. Each location cursor is moved by the operator to the respective feature on the image. The two dimensional transformation is then applied. The re-registration is performed and provides replication or interpolation of data between adjacent pixels. The previously defined measurement tools from the template can then be re-applied to the new image. Since the image is now identically registered with the original, no changes are required to the positions of the measurement tools and the data from each tool can be extracted automatically. Images can be differenced (subtracted) one from another with great accuracy and relative changes within successive images can be shown and measured. Variations in sensor positions can be compensated for and features' positions identified using values which relate directly to their physical location in space terms. Since it is not uncommon for such images to be distorted or non-linear in respect to their spatial orientation or aspect ratio, a digitised visual image can be used for the reference template and all re-alignment of the sensor images made to that image.

Custom printed reports can be made by linking image(s) and analysis results from the data files (spreadsheets), or directly from the images, into a wordprocessor. Specific document templates can be created in the wordprocessor to allow automated generation of pre-defined reports. In this way, details extracted from the image, including the colourised or monochrome image itself, can be transferred into a boilerplate text. An extensive database can be created from the data files (spreadsheets) to allow data trending to be carried out.

Fully automated image processing can also be carried out at the time of site inspection without the need to make a permanently stored image file. By way of example, the following procedure can be carried out: The image is frozen temporarily on screen in front of the operator. The reference file/spreadsheet for that particular subject is loaded and the position cursors shown on the frozen image. The position cursors are then moved onto their features by the operator. The image transformation then takes place. The measurement tools from the reference template file contains the tools used and their image positions and since the image has been transformed to occupy the same space as the original template image, will now apply to the correct location on the new image. The data is extracted automatically from the test image and filed for permanent record purposes or data analysis/trending. Since the relevant information has now been extracted from the image, the image itself can then be discarded and the observer can move to the next location to repeat the process.

It is of course to be understood that the invention is not intended to be restricted to the details of the above embodiment which are described by way of example only.

I claim:

1. A method of monitoring hot spots in electrical or electronic equipment using portable imaging equipment which moves from a first position to a second position comprising:

a) generating first and second images of the electrical or electronic equipment using said portable imaging equipment from said first and second positions respectively, b) determining coordinates of reference points on said first and second images, c) monitoring the temperature of a predetermined position or zone of said first and second images relative to the coordinates for the image, d) comparing each said monitored temperature with a respective predetermined reference temperature, e) determining any deviation between the determined coordinates of the reference points in said first and second images and predetermined coordinates therefor caused by non-coincidence of said first and second positions, and f) correcting for the deviation by a transformation of said second image while effecting the said monitoring of temperature of the predetermined position or zone so as to allow a direct comparison of temperature of said position or zone in said first and second images.

2. A method according to claim 1 which is performed with computer apparatus incorporating a screen on which an obtained image is visually displayed in conjunction with a cursor or pointer arrangement for locating the said reference points and establishing the coordinates thereof, on the displayed image.

3. A method according to claim 2 wherein said second image is automatically visually re-aligned on the screen, after the coordinates of the reference points have been established, to bring such reference points accurately into registration with the predetermined coordinates thereof.

4. A method according to claim 1 wherein a line is identified on said first and second images and variations in said temperature are calculated along said line.

5. A method according to claim 1 wherein the imaging equipment comprises infrared thermography equipment using an infrared sensor.

6. A method as claimed in claim 1 wherein said first and second images are represented in X, Y, Z coordinates.

7. A method of monitoring hot spots in electrical or electronic equipment using portable imaging equipment comprising:

a) generating a first image of the electrical or electronic equipment with portable imaging equipment at a first position of said portable imaging equipment, said portable imaging equipment comprising infrared thermography equipment using an infrared sensor, b) moving said portable imaging equipment from said first position to a second position, c) generating a second image of the electrical or electronic equipment at said second position, d) determining coordinates of reference points on said first and second images, e) monitoring the temperature of a predetermined position or zone of said first and second images relative to the coordinates for the image, f) comparing each said monitored temperature with a respective predetermined reference temperature, g) determining any deviation between the determined coordinates of the reference points in said first and second images and predetermined coordinates therefor caused by non-coincidence of said first and second positions, and h) correcting for the deviation by a transformation of said second image while effecting the said monitoring of temperature of the predetermined position or zone so as to allow a direct comparison of temperature of said position or zone in said first and second images.

8. A method according to claim 7 wherein a line is identified on said first and second images and variations in said temperature are calculated along said line.

9. A method as claimed in claim 7 wherein said first and second images are represented in X, Y, Z coordinates.

10. A method according to claim 7 which is performed with computer apparatus incorporating a screen on which an obtained image is visually displayed in conjunction with a cursor or pointer arrangement for locating the said reference points, and establishing the coordinates thereof, on the displayed image.

11. A method according to claim 10 wherein said second image is automatically visually re-aligned on the screen, after the coordinates of the reference points have been established, to bring such reference points accurately into registration with the predetermined coordinates thereof.

* * * * *